United States Patent [19]

Schaefer

[11] 4,451,584

[45] May 29, 1984

[54] MOLDING COMPOUND FOR MOLDING BODY PORTIONS AND PROCESS FOR PRODUCING THIS MOLDING COMPOUND

[76] Inventor: Philipp Schaefer, Oberstrasse 16, D-3000 Hannover 1, Fed. Rep. of Germany

[21] Appl. No.: 381,000

[22] Filed: May 21, 1982

[51] Int. Cl.$^3$ .................. B68G 1/00; B68G 11/04; C08L 27/08; C08L 83/04

[52] U.S. Cl. .................. 521/54; 523/109; 523/113; 523/115; 523/121; 524/506; 524/588

[58] Field of Search ............. 521/54; 523/109, 113, 523/115, 121; 524/506, 588

[56] References Cited

U.S. PATENT DOCUMENTS

| | | | |
|---|---|---|---|
| 3,082,527 | 3/1963 | Nitzsche et al. | 523/109 |
| 3,642,666 | 2/1972 | Bartl et al. | 521/54 |
| 3,696,090 | 10/1972 | Lampe | 523/121 |
| 3,850,864 | 11/1974 | Emerson | 523/109 |
| 3,864,181 | 2/1975 | Wolinski et al. | 521/54 |
| 4,000,108 | 12/1976 | Yokokawa et al. | 521/54 |
| 4,035,453 | 7/1977 | Hittmair et al. | 523/109 |
| 4,108,806 | 8/1978 | Cohrs et al. | 521/54 |
| 4,252,910 | 2/1981 | Schaefer | 521/145 |
| 4,320,076 | 3/1982 | Greenwood | 521/54 |

FOREIGN PATENT DOCUMENTS

| | | | |
|---|---|---|---|
| 716117 | 8/1965 | Canada | 521/54 |
| 29021 | 5/1981 | European Pat. Off. . | |
| 1629381 | 9/1975 | Fed. Rep. of Germany . | |
| 2519910 | 2/1976 | Fed. Rep. of Germany . | |
| 2036720 | 5/1977 | Fed. Rep. of Germany . | |
| 53-59728 | 5/1978 | Japan | 521/54 |
| 1091476 | 11/1967 | United Kingdom | 523/115 |
| 2026000 | 1/1980 | United Kingdom . | |

*Primary Examiner*—Ronald W. Griffin
*Attorney, Agent, or Firm*—Karl F. Ross; Herbert Dubno

[57] ABSTRACT

A molding compound for molding body portions preferably serves the purpose of producing a counterpart for the production of a model for making prostheses, particularly teeth prostheses or orthopaedic prostheses, or the purpose of cladding such prostheses for adapting same to a changed shape of body portions. This molding compound consists of a silicone containing pressure-elastic hollow microspheres the thin shell of which consists of a vinylidene chloride copolymer and the interior of which contains a gas. This silicone is initially liquid or pasty and, respectively, kneadable and solidifies after a certain time to a rubber-like consistency by adding a hardener, so that the molding compound reproduces the shape of the body portion to be molded.

7 Claims, No Drawings

MOLDING COMPOUND FOR MOLDING BODY PORTIONS AND PROCESS FOR PRODUCING THIS MOLDING COMPOUND

FIELD OF THE INVENTION

The invention relates to a molding compound for molding to a shape comforming to body portions, e.g. directly or indirectly by molding a model of these body portions, for example a plaster model of these body portions. The invention particularly relates to a molding compound for making a counterpart of teeth for producing artificial teeth or to a compound with which a teeth prosthesis can be underlaid for adapting this teeth prosthesis to a jaw changed in shape.

BACKGROUND OF THE INVENTION

Molding compounds for molding body portions are used in the field of dentistry for producing a counterpart of teeth and jaws required for making prostheses but are also used for underlaying such prostheses to adapt the same to the changing jaw. Thereby, a molding compound of pasty or kneadable consistency is put into a so-called spoon which is then pressed against the teeth and the jaw to be molded whereupon the molding compound is allowed to set or cure and subsequently the molding spoon is, together with the cured molding compound contained therein, pulled off the teeth and the jaw, the shape of the molding compound then corresponding to the shape of the body portions from which a counterpart has to be produced. Another field of application is the adaption of protheses for the deaf to the shape of the ear and in orthopedics where such molding compounds are used for producing a counterpart of a body portion required for making a prosthesis.

Molding compounds used up till now consist of a silicone in liquid or paste form or, respectively in a kneadable form and being cured by the addition of a hardener. The compound is then cured over a certain time to a rubber-like consistency. The term "silicone" means synthetic polymeric compounds in which silicon atoms are linked with interposition of oxygen atoms and in which the remaining valences of the silicon are saturated by hydrocarbon residues. Details referring to such silicones are for example given in Römpps Chemie-Lexikon, 7. edition/1975, Franck'sche Verlagshandlung W. Keller & Co., Stuttgart, volume 5, columns 3223 ff.

Recently common kneadable silicone compounds used in dentistry for producing counterparts of teeth and jaws contained a high proportion of inorganic fillers and had the drawback of high density and bad flowability or flow capacity. Such compounds must therefore be deformed by applying a substantial pressure and in spite thereof small details are not reproduced because these molding compounds can not penetrate into small cavities.

Working with the known molding compounds is difficult for the physician because these molding compounds must for the purpose of ease and rapidity of applying the molding compound into the molding spoon initially be kneadable and must not flow into the throat during molding operation and because these molding compounds must also mold or reproduce fine structures. Because the molding compound must not be liquid, incorporation of the hardener requires much skill and force and additionally there is only little mixing time at the disposal of the uses in view of the desired rapid cure of the molding compounds.

A further drawback of molding compounds containing inorganic fillers is the fact that their dilatancy exceeds their thixotropy on rapid movement. Dilatancy causes the molding compounds to rigidify during movement, which results in obstructing a rapid transport for example through a thin cross section and in making difficult an abrupt short-timed accommodation of the molding compound to a body portion.

OBJECTS OF THE INVENTION

It is an object of the present invention to provide a molding compound for making counterparts of body portions free from the drawbacks of known molding compounds.

It is a further object of the present invention to provide a molding compound for making counterparts of body portions and which has a high viscosity, a pasty and kneadable consistency, a low density, and substantially better flow characteristics under pressure than molding compounds known heretofore.

It is a further object of the invention to provide a molding compound for making counterparts of body portions and which has on rapid flow an increased thixotropy exceeding its dilatancy so that the compound is capable of penetrating into even small cavities and thus to reproduce even finest structures.

SUMMARY OF THE INVENTION

According to the invention I provide a molding compound for making counterparts of body portions which allows its liquid constituents to flow, when pressing the molding compound onto the body portion to be reproduced, to the surface of the compound so that this surface is enriched in a silicone compound of low viscosity. Furthermore, the invention provides a molding compound for making the counterpart of body portions which has the required elasticity on pressure stress and tension stress so that this compound can, after having been cross-linked by condensation reaction or addition reaction, without laterally yielding reduce its volume under pressure under the same conditions existing in liquid or kneadable condition and spontaneously and completely restores its shape on pressure release. This is of particular importance if the molding compound is used for producing counterparts of teeth because the cured or set molding compound must be capable of being pulled off of even barrel-shaped teeth but must show the shape of these teeth exactly even after having been pulled off these teeth.

The molding compound of the invention for making the counterpart of body portions requires a smaller amount of curing agent for hardening for a predetermined desired curing time as compared with molding compounds up till now and in which the curing agent or hardener can easier and more rapidly be distributed as long the silicone is in a kneadable condition.

More particularly the invention comprises a molding compound consisting of a silicone which is initially kneadable and contains a hardener, and pressure-elastic hollow microspheres within the shells consisting of a vinylidene chloride copolymer encapsulating a gas and of a diameter between 0.01 and 0.1 mm, the microspheres being present in the compound in an amount such that they constitute between 10 and 85% volume, preferably between 20 and 50% volume such that the molding compound has a density between 0.4 and 0.8.

The molding compound can be made by heating compact particles of vinylidene chloride copolymer containing a blowing agent to expand these particles into hollow microspheres having a diameter between 0.01 and 0.1 mm. The heating to form the microspheres is to a temperature exceeding 80° C. for approximately 10 minutes in a receptacle containing water or steam. The hollow microspheres are then removed from the receptacle and dried before being added to at least part of the silicone. Alternatively, at least part of the silicone of the compound is heated to a temperature in excess of 80° C. and compact particles of a vinylidene chloride copolymer containing the blowing agent are added to form the hollow microspheres in situ, whereupon the hardener is added.

SPECIFIC DESCRIPTION

Example 1

A starting mass of pasty to kneadable consistency consisting of a silicone was mixed with 25 percent by volume of pre-fabricated hollow microspheres. There were added microspheres of different diameter and the diameter was within the range of 0.01 to 0.1 mm. Subsequently the mixture obtained was mixed with 0.2 percent of a hardener or curing agent whereupon the mixture obtained was put into a molding spoon and pressed against the teeth and, respectively, the jaw, the shape of which had to be reproduced. Approximately 4 minutes later the compound having become set or cured within the molding spoon was pulled off the teeth and the jaw. Pulling off of the molding compound resulted in no difficulties also with teeth of greater thickness in their middle area than in their marginal area with which they were anchored within the jaw. In this case, the molding compound was subjected to compression when being pulled off the teeth but then again returned into the shape assumed on curing. 24 hours after removing the compound from the mold its shrinkage was approximately 0.2 percent. The hardness was approximately 75 Shore A.

The amount of hollow microspheres can be varied according to the requirement and can be within the range of 10 to 85 percent by volume. The amount of hollow microspheres added is preferably between 20 and 50 percent by volume. This corresponds to an amount of hollow microspheres added of 1 to 8 percent by weight, preferably 1 to 4 percent by weight. By adding hollow microspheres in an amount of 1 to 8 percent by weight, the density of the silicone compound is reduced for approximately 9 to 77 percent, for example from a density of 1.25 to a density between 1.14 and 0.29. Conveniently, the number of hollow microspheres added is such that the density of the molding compound is between 0.4 and 0.8. Such an amount of added microspheres provides the possibility to compress the molding compound for up to 50 percent of the volume of the hollow microspheres without expelling the gas enclosed within these microspheres so that on pressure release of an even non-crosslinked molding compound its volume is practically completely brought back to its starting volume. A molding compound containing microspheres in an amount of 20 percent by volume can thus be elastically compressed for approximately 10 percent by volume in a non-crosslinked condition.

If prefabricated hollow microspheres are mixed with the starting mass consisting of a silicone, these hollow microspheres are prefabricated prior to the mixing operation from compact particles containing an inflating agent. For this purpose, compact particles of a vinylidene chloride copolymer and containing an inflating agent are heated to a temperature exceeding 80° C. for approximately 10 minutes within a receptacle containing water or steam whereupon the inflated particles are removed from the receptacle and finally dried.

Example 2

100 g of a silicone compound are heated to a temperature of 150° C. Subsequently, there are stirred into the heated silicone compound 5 g of compact particles containing an inflating agent, said particles being, for example, available under the designation EXPANCEL and are, for example, available at the firm Kema-Nord in Sundvall, Sweden. Hollow microspheres produced therefrom are described in DE-OS No. 1 495 485 and in "Modern Plastics", August 1969, p. 55.

After approximately 1 minute hollow microspheres of various diameters have been formed in situ from the compact particles, said particles being equally distributed throughout the whole silicone compound. The diameter of these hollow microspheres was somewhat smaller than that of the prefabricated hollow microspheres used in example 1. Prior to incorporating the compact particles, the compound showed a density of 1.25 and a viscosity of approximately 40,000 cP as measured in a Broockfield-viscosimeter (LV4, n=6 revolutions per minute). The finished compound containing the hollow microspheres formed in situ showed a density of 0.55 and a viscosity of approximately 100,000 cP. This finished compound showed essentially thixotropic properties and could easily be transported under pressure action.

The further use of this molding compound was, after the addition of a curing agent or hardener, the same as described in example 1.

It is also possible to mix a silicone compound containing hollow microspheres produced therein in situ with the same silicone compound containing no hollow microspheres. Thereby, it has to be considered that such an amount of hollow microspheres be formed in situ within the first-mentioned compound that the final compound present after adding the silicone compound containing no hollow microspheres contains the desired proportion of hollow microspheres.

Preferred fields of application of a molding compound according to the invention are in the dentistry and in the orthopedics. In the field of dentistry, the molding compound according to the invention serves as a molding compound for producing a model representing the shape of the tooth and of the jaw of the patient. For this purpose, the counterpart of the teeth or the jaw can be directly molded on the patient. The molding compound can, however, also be used as a so-called duplicating compound with which the counterpart of an already existing model is produced. Furthermore a molding compound according to the invention is used in dentistry also for underlaying teeth prostheses in case the shape of the jaw supporting the teeth prosthesis has changed its shape and thus the shape of the teeth prosthesis has to be adapted to the changed shape of the jaw. In this case, a silicone adhesion promoter is applied, for example brushed onto the portion of the prosthesis to be underlaid and, respectively, to be clad whereupon the molding compound according to the invention is applied thereon in a still plastic and, respectively, kneadable condition. This molding compound is subsequently pressed against the jaw and allowed to set or cure so that the prosthesis is exactly adapted to the shape of the jaw and any change of the jaw, any gums atrophy or the like is considered.

Also in the field of orthopedics, the molding compound according to the invention can be used for producing counterparts of limbs to which a prosthesis has to be adapted or for underlaying and, respectively, cladding the interior of prostheses for exactly adapting same to the body portion. In this case, the mode of operation is the same as when underlaying these prostheses.

What I claim is:

1. A molding compound for molding body portions, said molding compound consisting of a silicone being initially liquid or pasty and, respectively, kneadable and solidifying to a rubber-like consistency after a certain time interval when having added a hardener, the silicone being added, prior to solidifying, with pressure-elastic hollow microspheres of a diameter between 0.01 and 0.1 mm, the thin shells of which consist of a vinylidene chloride copolymer and the interior of which contains a gas, the microspheres being present in the compound in an amount between 10 and 85 percent by volume.

2. A molding compound according to claim 1 wherein hollow microspheres of different diameters are added to the silicone.

3. A molding compound according to claim 1 wherein the hollow microspheres are added to the silicone in an amount between 20 and 50 percent by volume.

4. A molding compound according to claim 1 and having a density between 0.4 and 0.8.

5. A process for producing a molding compound consisting of a silicone being initially liquid or pasty and, respectively, kneadable and solidifying to a rubber-like consistency after a certain time interval, a hardener and hollow microsphere for molding body portions comprising the steps of:

producing hollow microspheres from compact particles containing an inflating agent by heating said particles;

adding the resulting hollow microspheres at least to a part of the silicone; and adding a hardener to the silicone so that the silicone is solidified to a rubber-like consistency after a certain time interval.

6. A process according to claim 5
wherein compact particles of vinylidene chloride copolymer containing an inflating agent are heated to a temperature exceeding 80° C. for approximately 10 minutes within a receptacle containing water or steam, whereby the hollow microspheres are formed from the compact particles;

the hollow microspheres are removed from the receptacle and dried;

the hollow microspheres are added to at least part of the silicone;

the hardener is added to the silicone containing the hollow microspheres, whereby the compound solidifies to a rubber-like consistency after a certain time interval.

7. A process for producing a molding compound consisting of a silicone being initially liquid or pasty and, respectively, kneadable and solidifying to a rubber-like consistency after a certain time interval, a hardener and hollow microsphere for molding body portions comprising the steps of:

heating at least part of the silicone or the liquid constituent of the molding compound to a temperature exceeding 80° C.;

subsequently stirring compact particles of a vinylidene chloride copolymer and containing an inflating agent into the heated silicone, whereby hollow microspheres are formed in situ; and adding a hardener to a silicone containing the hollow microspheres, whereby the compound solidifies to a rubber-like consistency after a certain time interval.

* * * * *